(12) United States Patent
Morgenstern et al.

(10) Patent No.: US 7,794,691 B2
(45) Date of Patent: Sep. 14, 2010

(54) RADIONUCLIDES FOR MEDICAL USE

(75) Inventors: Alfred Morgenstern, Karlsruhe (DE);
Christos Apostolidis, Heidelberg (DE);
Roger Molinet, Linkenheim (DE);
Klaus Luetzenkirchen, Hochstetten (DE)

(73) Assignee: The European Community, represented by the European Commission, Brussels (BE)

( * ) Notice: Subject to any disclaimer, the term of this patent is extended or adjusted under 35 U.S.C. 154(b) by 1672 days.

(21) Appl. No.: 10/875,182

(22) Filed: Jun. 25, 2004

(65) Prior Publication Data

US 2010/0189642 A1    Jul. 29, 2010

(51) Int. Cl.
*A61K 51/00* (2006.01)
*A61M 36/14* (2006.01)

(52) U.S. Cl. .................... 424/1.81; 424/1.11; 424/1.49; 424/1.65; 424/1.69; 424/9.1; 514/2

(58) Field of Classification Search ................ 424/1.11, 424/1.49, 1.65, 1.69, 1.81, 9.1; 514/2, 9
See application file for complete search history.

(56) References Cited

U.S. PATENT DOCUMENTS 5,922,302 A    7/1999    Goldenberg et al.

FOREIGN PATENT DOCUMENTS

| WO | WO 99/28450 | 6/1999 |
|---|---|---|
| WO | WO 02/05859 A2 | 1/2002 |
| WO | WO 02/22000 A2 | 3/2002 |

OTHER PUBLICATIONS

Dox et al (The Harper Collins Illustrated Medical Dictionary, 1993, p. 132).*
Golub et al (Science, 1999, vol. 286, pp. 531-537).*
J. M. Pagel, et al., "The use of radioimmunoconjugates in stem cell transplantation", Bone Marrow Transplantation, vol. 29, No. 10, XP-002320204, May 2002, pp. 807-816.
Richard M. C. Sutton, et al., "Comparison of the retention behavior of uranium and thorium on high-efficiency resin substrates impregnated or dynamically coated with metal chelating compounds", Journal of Chromatography A, vol. 816, No. 2, XP-004145858, Aug. 14, 1998, pp. 286-291.
Gjermund Henriksen, et al., "Thorium and Actinium Polyphosphonate Compounds as Bone-Seeking Alpha Particle-emitting Agents", Anticancer Research, vol. 24, No. 1, XP-009033741, Feb. 2004, pp. 101-106.
A. R. Peacocke, et al., "Binding of Calcium, YTTRIUM and Thorium to a Glycoprotein from Bovine Cortical Bone", Nature, vol. 211, No. 54, XP-008061919, Sep. 10, 1966, pp. 1140-1141.
S. P. Hassfjell, et al., "Bi-DOTMP: An Alpha Particle Emitting Bone-Seeking Agent for Targeted Radiotheraphy", Nuclear Medicine & Biology, vol. 24, No. 3, XP-004073582, Apr. 1997, pp. 231-237.
Frank Asaro, et al., "Alpha-Particle and Gamm-Ray Spectra on the $U^{230}$ Decay Series", Physical Review, vol. 104, No. 1, XP-002373672, Oct. 1, 1956, pp. 91-99.
A. Koua Aka, et al., "Reinvestigation of Decay Properties of Nuclei belonging to the $^{230}U$ Series using Continuous Radiochemical Separations", Radiochimica Acta, vol. 68, No. 3, XP-008061714, 1995, pp. 155-160.
Frank Stephens, Jr. et al., "Low-Lying 1-States in Even-Even Nuclei", Physical Review, vol. 96, No. 6, XP-002373673, Dec. 15, 1954, pp. 1568-1572.
W. H. A. Hesselink, et al., "Perturbations of Alpha-gamma Angular Correlations in the Decay of $^{230}U$ and $^{226}TH$", Z. Physik, vol. 247, No. 2, XP-008061887, pp. 161-165.
W. Kurcewicz, et al., "Collective States Fed by Weak $\alpha$-Transitions in the $^{230}U$ Chain", Nuclear Physics A, vol. A270, No. 1, XP-008061710, 1976, pp. 175-188.
N. Kaffrell, et al., "Collective States Fed by Weak Alpha Transitions in the $230_u$ and $232_u$ Chains", Proc. Int. Conf. Nucl. Struct. Spectrosc., vol. 1, XP-008061715, p. 117.
Michael Anderson, et al., "Mutations in the Tumor Suppressor Gene p53 in Human Liver Cancer Induced by $\alpha$-particles", Cancer Epidemiology Biomarkers & Prevention, vol. 4, No. 7, XP-002373674, Oct./Nov. 1995, pp. 765-770.

* cited by examiner

*Primary Examiner*—D L Jones
(74) *Attorney, Agent, or Firm*—Oblon, Spivak, McClelland, Maier & Neustadt, L.L.P.

(57) ABSTRACT

Methods of using Th-226 or mother radionuclides thereof, namely U-230 or Th-226, in medicine. These radionuclides are particularly appropriate for the treatment of human and/or non-human mammals, in particular for therapeutic, diagnostic (detection/imaging), prophylactic and pain palliation purposes. These radionuclides may be used in various forms for treatment and/or diagnostic purposes, in particular in cationic form or in the form of radioconjugates or bone-targeting complexes. Methods of making such radionuclides.

12 Claims, 4 Drawing Sheets

RADIONUCLIDES FOR MEDICAL USE

TECHNICAL FIELD

The present invention generally relates to radionuclides suitable for use in medicine.

BACKGROUND ART

The radiotherapeutic treatment of cellular disorders, including cancer and infectious diseases is widely documented in literature. A variety of methods have been developed in order to utilise radionuclides in radiotherapy, including targeted radiotherapy, pre-targeted radiotherapy and the use of radionuclides in the form of bone-seeking complexes.

Targeted alpha therapy (TAT) is a site directed treatment modality for cellular disorders, including cancer and infectious diseases, using alpha radiation to selectively destroy targeted cells, e.g. tumour cells, fungal cells or bacteria. The principle of TAT is based on the coupling (also referred to as binding or linking) of alpha-emitting radionuclides to targeting moieties, e.g. monoclonal antibodies or peptides, that recognise a structure in, on or near a target. Due to the short path length of alpha particles in human tissue (<100 μm), TAT has the potential of delivering a highly cytotoxic radiation dose to targeted cells, while limiting the damage to surrounding healthy tissue. Several pre-clinical and clinical studies have shown the feasibility of TAT for the treatment of various types of cancer [Ref. 9, Ref. 11, Ref. 1, Ref. 16, Ref. 12] and infectious diseases [Ref. 5].

Several reports [Ref. 15, Ref. 17, Ref. 18] have shown the potential of pre-targeting techniques for radiotherapy. Pre-targeting techniques, typically using the high affinity of avidin-biotin binding, show the potential for the rapid and selective delivery of radionuclides to target sites leading to the reduction of radiation delivered to normal tissues. Pre-targeted radiotherapy is therefore especially well suited for applications using short-lived radionuclides. A promising approach for pre-targeted radiotherapy, as reported by the NeoRx Corporation (Seattle, Wash., USA) consists of three steps. In step 1, an antibody-streptavidin (SA) conjugate is administered intravenously and allowed to target and accumulate in the tumour. In step 2, a synthetic biotinylated clearing agent is administered to clear unbound antibody-SA from the circulation in vivo. The resultant complexes are rapidly cleared into the liver and metabolized. In step 3, the radionuclide is delivered to the tumour site by administration of radiolabeled biotin, a low molecular weight molecule that rapidly reaches and binds to antibody-SA pre-localized at the tumour site [Ref. 18].

Other known variants of pre-targeted radiotherapy are:
- the injection of a biotinylated monoclonal antibody in the first step, followed by the administration of avidin to avidinylate the tumour and by injection of radiolabelled biotin in the third step [Ref. 25].
- a 5-step strategy as follows: (1) injection of biotinylated antibody; (2) administration of avidin to clear biotinylated antibody from circulation; (3) injection of streptavidin to avidinylate the tumour; (4) clearing of circulating streptavidin by biotinylated albumin and (5) injection of radiolabelled biotin [Ref. 26]
- the use of bi-specific antibodies for tumour targeting with one binding site and accumulation of a radiolabelled peptide by the second binding site [Ref. 22].

A further application of alpha-emitting radionuclides for radiotherapy is the administration of bone-targeting complexes of alpha-particle emitting radionuclides in therapeutical, prophylactic or pain-palliating amounts, e.g. for the treatment of calcified tumours, bone tumours, bones, bone surfaces and soft tissues as described e.g. in WO 03/105762. By bone-targeting it is meant that the radionuclide complex distributes preferentially to the bone as opposed to soft tissue organs, in particular liver, spleen and kidney.

Bone metastases are frequent in cancer patients. Chemotherapy, external radiotherapy or hormone therapy induce temporary responses, but ultimately most patients relapse. As a result, new therapies are required to inhibit tumour progression and to relieve pain.

The use of radionuclides for the treatment of bone metastases in cancer patients seems to be promising. P-32-orthophosphate, Sr-89-chloride, Sm-153-EDTMP (ethylenediaminetetramethylene phosphonic acid), Re-186-HEDP (hydroxyethylidene diphosphate) and Re-188-HEDP have already been used in clinical trials with benefits in palliation of osseous metastases [Ref. 10]. The bone-seeking properties of the nuclides are based on their elemental nature or on the chemical properties of an attached ligand. They are preferentially incorporated into bony lesions undergoing new bone formation compared with normal bone. Administered intravenously as a systemic approach, the radionuclides offer the opportunity to treat several lesions simultaneously, as most patients with skeletal metastases have multiple localizations.

The effects of bone-targeting radiopharmaceuticals based on beta-emitters include, due to their long radiation range, a significant exposure of the bone marrow leading to hematological toxicity. Alpha-emitters are a possible alternative. At-211 linked to bisphosphonates [Ref. 21], Bi-2,2-DOTMP [Ref. 19], Ra-223 [Ref. 20] and Ra-224 [ref. 14] have already been evaluated as bone-seeking agents.

Today, a main impediment for the use of alpha-emitters in radiotherapy is the limited availability of suitable alpha-emitting radionuclides in sufficient quantities for widespread medical use. Among the alpha-emitters presently considered for radiotherapy, including Tb-149, Ra-223, At-211, Bi-213, Ac-225 and others, Bi-213 (half-life $T_{1/2}$=46 min), available through the decay chain of Ac-225 ($T_{1/2}$=10 days), is presently the most promising. The bottleneck for the widespread use of the Ac-225/Bi-213-pair in radiotherapy has been the limited availability of the mother radionuclide Ac-225. Presently, Ac-225 can be obtained only in limited quantities (approx. 1 Ci per year) by radiochemical separation from Th-229 sources available at the Institute for Transuranium Elements in Karlsruhe, Germany and Oak Ridge National Laboratory, USA [Ref. 2, Ref. 4].

These facts severely limit the progressing of studies investigating TAT.

To further advance the application of TAT, alternative radionuclides need to be found that can be produced in technical simple way in sufficient quantity and purity, that can be combined to targeting moieties in a stable manner, and that have decay characteristics that allow their use in humans.

OBJECT OF THE INVENTION

The object of the invention is to provide alternative radionuclides that are suitable for medical use.

GENERAL DESCRIPTION OF THE INVENTION

According to the present invention, the use of thorium-226 (Th-226) or a mother radionuclide thereof is proposed for medical applications. As mother radionuclides, uranium-230 (U-230) and actinium-226 (Ac-226), which mainly decay in the Th-226 daughter through a single radioactive decay, are particularly preferred.

The present invention more specifically proposes the use in medicine of U-230, Ac-226 and of Th-226 obtained by radioactive decay of U-230 or Ac-226, in particular for Targeted Alpha Therapy. These radionuclides are particularly well suited for use on humans as wells as on non-human mammals, especially due to their decay characteristics (radiations, half-life), chemical stability under physiological conditions and their ability to be linked to biological carrier molecules. Furthermore, there are various production routes of U-230 and Ac-226, and thus of Th-226, which ensures the production of these radionuclides in sufficient quantity and purity.

It will be appreciated that Th-226 is a short-lived radionuclide ($T_{1/2}$=31 min) that has favourable decay characteristics and emits a plurality of alpha-particles with a cumulative energy of 27.7 MeV, being thus capable of delivering a highly cytotoxic dose to targeted cells. Furthermore, it is to be noted that thorium as a tetravalent actinide (Th(IV)) forms extremely stable complexes with many chelating ligands, which allows the stable binding of the radioisotope to biological carrier molecules via chelating moieties. In addition, Th-226 emits gamma rays that do not require extensive shielding and that are in fact suitable for imaging of the biodistribution of the nuclides in the body. This can typically be done by detecting the emitted gamma rays. Finally, the alpha-emitting daughter nuclides of Th-226 have very short half-lives, which strongly limits the dislocation of the daughter nuclides away from the target sites therefore sparing surrounding healthy tissues.

Th-226 is thus a radionuclide that is particularly well suited for use in medicine, especially as radiotherapeutic and/or diagnostic agent. Theoretically, any radionuclide susceptible to decay into Th-226 and having a half-life ranging from one day to several weeks may thus be of interest as mother radionuclide. However, U-230 and Ac-226 are particularly preferred mother radionuclides since they have well suited decay characteristics and chemical properties, which make them interesting for use in medicine.

The present invention provides an improved alternative to the Ac-225/Bi-213-pair, which is of widespread use today in TAT. Indeed, the U-230/Th-226-pair can be used in a similar fashion than the actinium/bismuth-pair and thereby provides the advantages of pure alpha-emitters with high cumulative energy providing a high cytotoxic dose to targeted cells as well as allowing imaging of the biodistribution of the nuclides in the body. As for Th(IV), U(VI) is a very stable oxidation state of uranium under physiological conditions, which allows stable binding to biological carrier molecules. Furthermore, the production of U-230/Th-226 can be carried out through irradiation of e.g. natural, low radioactive Th-232. The irradiation of this low-radioactive material can be technically realised more easily than the irradiation of highly radioactive Ra-226, which is used for producing Ac-225. When using U-230 for the production of Th-226, U-230 ($T_{1/2}$=20.8 days) is typically fixed on a radionuclide generator (e.g. comprising extraction chromatographic material or ion exchanger) that allows the selective elution of Th-226. In this connection it is to be noted that the half-life of U-230 (approx. twice as long as the half-life of Ac-225) allows the preparation of a U-230/Th-226 radionuclide generator with a life time exceeding several weeks, thus facilitating the preparation and shipment of the generator as well as its use in hospitals. However, U-230 can also be used directly for treatment.

The other preferred mother radionuclide Ac-226 has a half-life of 29 h and decays through $\beta^-$ emission with a branching ratio of 83% to Th-226. Due to the longer half-life of Ac-226 compared to Th-226, it can be used to target cells that are less readily accessible than in the case of using Th-226. Upon administering to a patient, the decay of Ac-226 will produce in situ (e.g. in the body) short-lived Th-226 with its favourable decay characteristics and the emission of multiple alpha-particles, resulting in the delivery of a high cytotoxic dose to targeted cells. A further advantage of using Ac-226 as in situ generator of Th-226 lies in the decay properties of Ac-226 as it decays mainly through emission of a $\beta^-$ particle and through electron capture. In this decay mode the recoil energy affecting the decaying Ac-226 atom is lower than in the case of emission of e.g. an alpha-particle, whereby the probability that the daughter nuclide Th-226 will remain within the chelating moiety and close to the target cell is increased. Ac-226 can thus be used directly or as a source (generator) radionuclide for the production of Th-226, in which case it may be fixed on a radionuclide generator (e.g. comprising a column of extraction chromatographic material or ion exchanger) that allows the selective elution of Th-226.

It thus appears that Th-226, U-230 and Ac-226 are radionuclides that are particularly well suited for medical use, in particular for therapy and diagnosis/detection as well as for prophylaxis and pain palliation. This means that these nuclides are adapted i.a. for targeted or pretargeted alpha therapy, in particular alpha-immunotherapy, but also for bone treatment. As Th-226 is preferably obtained through radioactive decay of U-230 or Ac-226, these two radionuclides can either be directly used for medical applications or used as a source for the production of Th-226, e.g. by elution from a generator.

For the treatment of soft tissues, Th-226 or the mother radionuclide, especially U-230 or Ac-226, is preferably linked to target-selective biological carrier molecules that recognise a structure in, on or near the target and thus will permit the delivery of the radionuclides to the targeted tissues.

Accordingly, the present invention provides a radioconjugate for medical use, wherein the radioconjugate comprises Th-226 or a mother radionuclide thereof, preferably U-230 or Ac-226, bound to a targeting moiety having binding specificity for a target moiety associated with a target site.

As is well known in the field of TAT, the targeting can be accomplished by aiming the targeting moiety directly to the wanted site (direct targeting), but it may also be directed to a target moiety which is pre-localised on the wanted site (so-called pretargeting).

For direct targeting, the targeting moiety is thus selected to recognise a structure (the target moiety) in, on or near a target site. Such targeting moiety may typically be a target-selective biological carrier molecule selected from antibodies, monoclonal antibodies, peptides and fragments or derivatives thereof.

For radioimmunotherapy, the targeting moiety may preferably be a monoclonal antibody, or a fragment or derivative thereof. Preferably, such a monoclonal antibody is a human or a humanized antibody to prevent immunologic reactions to the antibody.

Of course, fragments and/or derivatives of the targeting moieties can also be used, as long as they retain a substantial amount of target specificity.

Another preferred targeting moiety is formed by a ligand for a cell surface receptor or a fragment or derivative of such a ligand. Examples of such ligands are agonists or antagonists of pharmacologically active receptors.

If desired, a number of radionuclides can be coupled to a carrier which is also bound to a targeting moiety. This permits to increase the number of radionuclides delivered to a site.

Pretargeting typically offers an advantage over direct targeting when the specificity of the targeting moieties is not sufficient. By using a first localizing moiety followed by a second one coupled to the cytotoxic radionuclide, the cytotoxic doses delivered to non-targeted sites can be lowered significantly. In such a case, the radionuclides are typically connected to low molecular weight molecules, such as e.g. biotin, that rapidly deliver the radioisotope to pre-localized antibody conjugates such as e.g. avidin-based compounds (e.g. streptavidin). Hence, a radioconjugate for pre-targeted alpha therapy typically comprises a targeting moiety that has binding specificity for a target moiety that has been pre-localised at (in, on or near) a target site.

The present invention also proposes a method for producing a radioconjugate, wherein a radionuclide is bound to a targeting moiety, this radionuclide being Th-226 or a mother radionuclide thereof. For the production of a radioconjugate including Th-226, the latter is preferably obtained by selective elution from a radionuclide generator comprising a separation column (e.g. extraction chromatographic material or ion exchange resin) loaded with mother radionuclides of Th-226, in particular U-230.

According to another aspect of the invention, a bone-targeting complex of a radionuclide is proposed, wherein the radionuclide is Th-226 or a mother radionuclide thereof, preferably U-230 or Ac-226. In the complex of the invention, Th-226 is preferably obtained through radioactive decay of U-230 or Ac-226.

By bone-targeting (also called bone-seeking), it is meant that the radionuclide complex distributes preferentially to the bone as opposed to soft tissue organs. Any chelating and/or complexing agents having an affinity to the bones can be used to form the complex of the invention. Phosphonic acid complexing agents, especially biphosphonate and polyphosphonates, are particularly preferred.

As an example, the complex of the invention can be used for prophylactic cancer treatment by delivering a focused dose to bone surfaces in patients with a high probability of having undetected micrometastases at the bone surfaces. Another example of its potential use would be in the treatment of painful osseous sites in a similar fashion as the current treatments with β and electron emitting radiopharmaceuticals for bone pain palliation.

Viewed from another aspect the invention proposes the use of Th-226 or a mother radionuclide thereof in the manufacture of a radiopharmaceutical. The radiopharmaceutical preferably includes as radionuclide Th-226 obtained through radioactive decay of U-230 or Ac-226; or U-230 or Ac-226. The term radiopharmaceutical herein shall mean any medicinal product which, when ready for use, contains one or more radionuclides included for a medicinal purpose (including therapy and diagnostic (by detection/imaging).

The present invention thus also concerns radiopharmaceuticals including Th-226 or a mother radionuclide thereof, in particular U-230 or Ac-226. Depending on the applications, the radionuclides may be combined to form constructs such as radioconjugates or bone-targeting complexes. Furthermore, the radionuclides can be used in the cationic form to exploit their intrinsic affinity to particular tissues, as is for example the case with U-230, which has a particular affinity for calcified tissues.

The radiopharmaceutical of the invention may of course comprise one or more physiologically acceptable carrier and/or excipient and/or diluent. In addition, the radiopharmaceutical may comprise a scavenging agent, as is conventional in the art.

For the preparation of the radioconjugates, the coupling of Th-226, Ac-226 and/or U-230 to the targeting moiety can be done in any suitable way, as long as the target specificity of the targeting moiety is not substantially reduced. Suitable complexing or chelating agents that can be used to bind Th-226, Ac-226 and/or U-230 to targeting moieties such as biological carrier molecules (e.g. monoclonal antibodies, humanized antibodies, antibody fragments or peptides) or carrier molecules for pre-targeted radiotherapy (e.g. biotin) are widely described in the literature.

When U-230 is used in targeted or pre-targeted radiotherapy, preferentially a chelating agent should be used that binds U-230 as well as its daughter nuclide Th-226 in a stable manner, in order to minimise the dislocation of Th-226 from the target cell following its formation through the decay of U-230 in situ. Possible chelating agents that can be used to bind uranium and thorium include multidentate ligands containing catecholate, catecholamide or hydroxy-pyridinone units as described in [Ref. 7], e.g. 5-LIO(Me-3,2-HOPO), 5-LICAM(S), 3,4,3-LI(1,2-HOPO) as described in [Ref. 6] and 5-LI(Me-3,2-HOPO) [Ref. 7].

Analogously, when Ac-226 is used in targeted or pre-targeted radiotherapy, preferentially a chelating agent should be used that binds Ac-226 as well as its daughter nuclide Th-226 in a stable manner, in order to minimise the dislocation of Th-226 from the target cell following its formation through the decay of Ac-226 in situ.

Preferred chelating agents are listed below:
DTPA (diethylenetriaminepentaacetic acid) and its derivatives (e.g. benzyl-DTPA, MX-DTPA (tiuxetan), cyclohexyl-DTPA), preferentially for chelation of thorium;
DOTA (1,4,7,10-tetraazacyclododecane-N,N',N'',N'''-tetraacetic acid) and its derivatives, preferentially for chelation of actinium;
HEHA (1,4,7,10,13,16-hexaazacyclooctadecane-N,N',N'', N''',N'''',N'''''-hexaacetic acid) and its derivatives, preferentially for chelation of actinium and thorium;
OHEC (octaazacyclohexacosane-1,4,7,10,14,17,20,23-octaacetate) and its derivatives, preferentially for chelation of actinium and thorium;
multidentate ligands containing catecholate, catecholamide or hydroxypyridinone units as described in [Ref. 7], e.g. 5-LIO(Me-3,2-HOPO), 5-LICAM(S), 3,4,3-LI (1,2-HOPO) as described in [Ref. 6] and 5-LI(Me-3,2-HOPO) [Ref. 7];
calixarene systems, crown ethers;
molecules that are studied as sequestering agents for tri-, tetra- and hexavalent actinides as described by Gordon et al. [Ref. 7].

The present invention thus generally concerns the use of Th-226 or mother radionuclides thereof for the treatment of human and/or non-human mammals, in particular for therapeutic, diagnostic (detection/imaging), prophylactic and pain palliation purposes. Depending on the applications, these radionuclides may be used in various forms for treatment and/or diagnostic purposes, in particular in cationic form or in the form of radioconjugates or bone-targeting complexes. Especially contemplated applications for the radiopharmaceuticals of the invention or of compounds using U-230, Th-226 or Ac-226 are listed below. This is a non-exhaustive list of diseases that can be treated using radiopharmaceuticals of the invention (i.e. including U-230, Th-226 or Ac-226) and for which preferred targeting moieties are indicated.

acute and chronic leukemias (e.g. treatment of acute myeloid leukemia using radioconjugates with anti-CD33 or anti-CD45 as targeting moiety; treatment of acute T-lymphoblastic leukemia using radioconjugates with anti-CD25 as targeting moiety; treatment of acute or chronic lymphocytic leukemia using radioconjugates with anti-CD52 (Campath) as targeting moiety; treatment of B-cell leukemias using radioconjugates with anti-CD22 as targeting moiety);

malignant lymphoma (e.g. treatment of Non-Hodgkin's lymphoma using radioconjugates of anti-CD19, anti-CD20, anti-CD22 or anti-CD45 antibodies or anti-HLA-DR as targeting moiety; treatment of Hodgkin's lymphoma using anti-CD30 as targeting moiety);

multiple myeloma (e.g. using radioconjugates comprising anti-IL-6 as targeting moiety);

gastric cancer (e.g. locoregional therapy using radioconjugates having as targeting moiety: d9Mab targeting HSC45-M2 human gastric cancer cells expressing d9-E-cadherin, 17-1A or anti-EGFR);

colon cancer (using anti-VEGF as targeting moiety);

colorectal cancer (e.g. using radioconjugates having as targeting moiety: CC49 scFvSA antibody-streptavidin fusion protein, anti-EGFR, anti-CEA);

liver cancer;

pancreatic cancer (e.g. using radioconjugates having as targeting moiety the c595 antibody targeting the MUC-1 receptor);

thyroid cancer (targeting moiety: MN-14);

breast cancer (targeting moiety: anti-HER1, anti-HER2/neu, anti-EGFR);

ovarian cancer (e.g. locoregional treatment using HEA antibody targeting the Epcam antigen, anti-L6);

prostate cancer (e.g. c595 targeting the MUC-1 receptor, J591, plasminogen activator inhibitor PAI-2, anti-PAP);

bladder cancer;

lung cancer (e.g. vascular targeting using radioconjugates with monoclonal antibodies; small cell lung carcinoma: N901-bR, anti-EGFR);

melanoma (e.g. intralesional therapy using radioconjugates comprising as targeting moiety: 9.2.27 antibody, anti-p97, anti-p240);

brain tumours, in particular treatment of tumor tissue before and/or after surgical brain tumour removal (e.g. using as targeting moiety D-Phe1-Tyr3-octreotide);

conjugation with angiogenesis inhibitors (e.g. using as targeting moiety: anti-alpha-V/beta-3, anti-VEGF);

conditioning regimes prior to stem cell transplantions (autologous or allogenic);

antimicrobial therapy, including fungal and bacterial infections (e.g. treatment of *streptococcus pneumoniae* infections using a targeting moiety: pneumococcal capsular polysaccharide 8 specific human antibody D11; treatment of *cryptococcus neoformans* infections using as targeting moiety: polysaccharide specific MAb 18B7 antibody);

all other diseases or cellular disorders where targeted or pre-targeted radiotherapy is applicable; and the treatment of calcified tissues using bone-targeting complexes of U-230, Th-226, Ac-226 or mixtures of these radionuclides for radiotherapy in therapeutical, prophylactic or pain-palliating amounts, e.g. for the treatment of calcified tumours, bone tumours, bones, bone surfaces and soft tissues, as single agents or in combination with: chemotherapy, hormones (androgens, parathormone—aimed to increase the incorporation into osseous metastases) or colony-stimulating factors.

Viewed from another aspect, the present invention also provides a method providing targeted radiotherapy to a pathological target site in a mammal comprising the steps of:

providing a radiopharmaceutical as defined above; and administering to said mammal a sufficient amount of said radiopharmaceutical to produce a radiotherapeutic effect at the pathological target site.

Furthermore, viewed from another aspect, the present invention provides a method for detecting a target site in a mammal, comprising:

providing a radiopharmaceutical as defined above; and administering said radiopharmaceutical to said mammal to effectuate specific binding of said radiopharmaceutical to said target site and detecting radiations originating from said radiopharmaceutical.

The nature of the radiations to be detected depend on the radionuclides. Th-226 emits gamma rays which can be detected by conventional techniques. Radiations originating from Ac-226 radiopharmaceuticals (Ac-226 is a positron emitter) can be detected using, the well known technique of positron emission tomography (PET).

According to still another aspect of the invention, a method for the ex-corpore treatment of human blood cells incorporating tumor cells is proposed, wherein the cells are mixed ex-corpore with a radioconjugate as defined above, and after an incubation period a purging of the blood cells is performed.

As already mentioned, an important aspect of the medical use of Th-226 is the availability of this radionuclide in sufficient amounts. In the present invention, Th-226 is preferably obtained by radioactive decay of U-230 or Ac-226.

A prior art method of producing U-230 has been described by Koua Aka et al. [ref. 13] and is based on the irradiation of Th-232 by protons. According to the reaction Th-232(p,3n) Pa-230, the β emitting isotope Pa-230 is formed, which decays into U-230 with a branching ratio of 8.4%. Taking into account the branching ratio and the half-lives of Pa-230 ($T_{1/2}$=17.4 d) and U-230 ($T_{1/2}$=20.8 d), the theoretical amount of U-230 that can be produced in this manner is limited to 3.37 wt. % of the amount of Pa-230 initially produced by the irradiation.

The present invention also provides a process for producing U-230, wherein a target of Th-232 is irradiated with deuterons. The reaction involved is this process is Th-232(d,4n)Pa-230, which also leads to formation of Pa-230, the latter decaying into U-230. Production yields similar to those obtained with proton irradiation [Ref. 13] can be expected. The energy of the deuteron is preferably adjusted so that the energy incident on the Th-232 target is between 20 and 35 MeV.

Viewed from another aspect, the present invention provides a further method for producing U-230 from Th-232, wherein the target of Th-232 is irradiated with helium nuclei. This process permits the direct production of U-230 according to the reaction Th-232($\alpha$,6n)U-230. The energy of the helium particles is preferably adjusted such that the energy incident on Th-232 is between 50 and 70 MeV, more preferably between 53 and 65 MeV. Taking into account the theoretical cross sections (using ALICE code) of the reactions Th-232(p,3n)Pa-230 (1260 mb at 22 MeV) and Th-232($\alpha$,6n) U-230 (1000 mb at 57 MeV), and also taking into account that U-230 is produced directly using the latter reaction, overall a 23.6-fold enhancement of production yield can be expected using the irradiation of Th-232 by helium particles compared to the current state-of-the-art method by Koua Aka et al. [Ref. 13].

It is to be noted that for the production of U-230 by irradiation of Th-232, preferably thorium metal will be used as target material, but also thorium targets prepared by electrodeposition or thorium oxide or other suitable thorium materials can be used. During irradiation, the Th-232 target material is preferably placed in a capsule and/or any other suitable sealed container, e.g. made of silver or aluminium and cooled by a closed water circuit. Conventional chemical separation techniques can be used for the separation of uranium from the irradiated target material.

An appreciable aspect of these production routes starting from Th-232 is that the targets may simply be pieces of natural metallic thorium (e.g. disks or plates). The low radioactivity of thorium facilitates the preparation, handling and transport of the target material and thus globally simplifies the irradiation procedures.

The present invention also provides a process for producing U-230, wherein a target of protactinium-231 is irradiated with hydrogen isotope nuclei. The present process allows the direct production of U-230, and is thus more interesting than the conventional production route through the reaction Th-232(p,3n)Pa-230, where U-230 is produced only as a decay product of Pa-230 with a maximal theoretical yield of 3.37 wt. % relative to the amount of Pa-230 produced.

In a first embodiment, the Pa-231 target is irradiated with protons to carry out the following reaction: Pa-231(p,2n)U-230. The protons preferably have an incident energy in the range of 10 to 25 MeV, more preferably between 13 and 17 MeV.

In a second embodiment, the Pa-231 target is irradiated with deuterons to carry out the following reaction: Pa-231(d,3n)U-230. The deuterons preferably have an incident energy between 10 and 25 MeV, more preferably between 18 and 21 MeV.

These preferred energy ranges for protons and deuterons permit to maximise and enhance the production yield of U-230 with respect to the other isotopes. The present method can be carried out in a cyclotron, in which the proton or deuteron energy is adjusted so as to have an incident energy in the preferred energy ranges.

During irradiation, the Pa-231 target, preferably in the form of protactinium oxide or metal or protactinium prepared by electrodeposition, is advantageously contained in a sealed capsule and/or other appropriate container. Furthermore, after irradiation uranium is preferably chemically separated from the irradiated target of Pa-231. This chemical separation can be performed using ion exchange, extraction chromatography and/or sorption to silica gel.

It will be appreciated that the direct production of U-230 by proton or deuteron irradiation of Pa-231 according to the present method is approx. 15 and 27 times, respectively, more efficient than the current state-of-the-art method for the production of U-230 from Th-232. Therefore, the present method permits a significant increase in the amounts of U-230/Th226 that can be made available for pre-clinical and clinical studies. Additionally, since a significant cost factor in the production of radioisotopes in a cyclotron is related to the irradiation time required, the production method of the invention can lead to a significant reduction of production costs.

The present invention thus proposes a number of processes for the production of U-230, which are advantageous in terms of productivity. These methods will thus permit sufficient production of U-230 for implementation of TAT with the U-230/Th-226 pair.

It is to be noted that the irradiation of Th-232 with protons or deuterons can also lead to the production Ac-225, depending on the proton or deuteron energies. Hence, radionuclides for U-230/Th-226 based TAT but also for Ac-225/Bi-213 based TAT can be provided.

Turning now to a further aspect of the invention, a method for producing actinium-226 is proposed, wherein a target of radium-226 (Ra-226) is irradiated with hydrogen isotope nuclei. This method allows the direct production of Ac-226 by irradiation of Ra-226 with deuterons or protons, e.g. in a cyclotron. Depending on the energy of the incident irradiating beam, high purity levels can be achieved, which is of importance for medical applications.

In a first embodiment, the Ra-226 target is irradiated with protons to carry out the following reaction: Ra-226(p,n)Ac-226. The protons preferably have an incident energy in the range of 5 and 15 MeV, more preferably between 8 and 12 MeV.

In a second embodiment, the Ra-226 target is irradiated with deuterons to carry out the following reaction: Ra-226(d,2n)Ac-226. The deuterons preferably have an incident energy between 5 and 15 MeV, more preferably between 10 and 12 MeV.

These preferred energy ranges for protons and deuterons permit to maximise and enhance the production yield of U-230 with respect to other isotopes. The present method can be carried out in a cyclotron, in which the proton or deuteron energy is adjusted so as to have an incident energy in the preferred energy ranges.

In the present method, Ra-226 target material is preferentially in the form of radium chloride, radium carbonate, radium sulfate or radium prepared by electrodeposition. To facilitate the handling of the highly toxic Ra-226 target material, the latter is advantageously placed in a sealed capsule of silver or aluminium. The capsule provides a leak-free container for the highly toxic Ra-226 and allows target processing after irradiation while preventing introduction of impurities into the medical grade product and avoids the introduction of undesired cations which would interfere with the chelation of the radionuclides.

After irradiation, actinium is preferably chemically separated from the irradiated target of Ra-226, e.g. using ion exchange or extraction chromatography.

As already mentioned, Th-226 as used in the present invention is preferably obtained from radioactive decay of U-230. Therefore, the U-230 mother radionuclide (or cow) is preferably loaded on a generator comprising an appropriate separation medium. The recovery (or milking) of Th-226 is then carried out by selective elution at predetermined time intervals, similarly to the milking of Bi-213 from a generator loaded with the Ac-225 cow. A variety of materials are known in the art for the separation of actinides and can be used for the preparation of a U-230/Th-226 generator, such as extraction chromatographic resin or ion exchange material.

However, a particularly preferred material for the preparation of a U230/Th-226 generator is the TEVA® resin (TEVA is a registered trademark of Eichrom Technologies Inc., USA).

Accordingly, the present invention proposes the use of TEVA® resin in the preparation of radiopharmaceuticals comprising Th-226, wherein Th-226 is obtained by elution from a generator comprising TEVA® resin initially loaded with U-230. Silica gel is advantageously used as inert support material for the TEVA resin. This allows to increase the radiation resistance of the generator material and minimise its radiolytic degradation. Th-226 can be eluted from the generator using 6 M hydrochloric acid with a yield of approx. 90% in 4-6 column bed volumes, while U-230 remains on the generator. A peristaltic pump can be used for the elution of the generator to facilitate the automation of the elution process.

The present invention also proposes a method for preparing Th-226 for use in medicine, the method comprising the steps of:

providing a solution comprising mother radionuclides of Th-226;

passing the solution over an appropriate separation medium to load it with the mother radionuclides of Th-226; and recovering Th-226 by elution from said separation medium.

The separation medium preferably comprises extraction chromatographic material or ion exchange material. The term elution is used herein indifferently for the separation of Th-226 from the ion exchange material as well as for the separation of the Th-226 by extraction chromatography. These techniques are conventional in the art for actinides separation and do not need further explanation as to their implementation.

In a preferred embodiment, a solution comprising hydrochloric acid and U-230 is prepared and passed over the separation column to load it with U-230. The elution of Th-226 is then carried out with a hydrochloric acid solution at selected time intervals. Preferred concentration of hydrochloric acid for both the loading and elution steps is 6 M. In this embodiment, the separation column preferably comprises extraction chromatographic material (such as TEVA® resin) and advantageously silica gel as inert support material.

It remains to be noted that the production of Th-226 in a radionuclide generator can easily be automated. Different types of automated radionuclides generators have been proposed before and can be adapted to operate according to the present method, i.e. with U-230 or Ac-226 as mother radionuclide and preferably featuring a separation column comprising TEVA® resin and silica gel.

More generally, it should be noted that the practical implementation of radiotherapy and/or imaging using Th-226 or mother radionuclides thereof can benefit from the technical developments that have already been achieved in the field of TAT using the Ac-225/Bi-213 pair. Indeed, most of the apparatuses that are used for TAT with Ac/Bi can be relatively easily adapted for use with the presently proposed radionuclides. This is another advantageous aspect of the present invention since the its implementation can rely on automated procedures, which is most appreciable for the users.

BRIEF DESCRIPTION OF THE DRAWINGS

The present invention will now be described, by way of example, with reference to the accompanying drawings, in which.

DETAILED DESCRIPTION OF PREFERRED EMBODIMENTS

The present invention proposes the use of the radionuclide Th-226 as well as mother radionuclides of Th-226 for medical purposes. Among the mother radionuclides of Th-226, U-230 and Ac-226 are particularly preferred for their advantageous properties.

The set of radionuclides comprising Th-226, U-230 and Ac-226 has been found to be optimally suited for use in medicine. In the following, the use of these three radionuclides in the medical field will be described in more detail. Their favourable decay characteristics, their use in the manufacture of radiopharmaceuticals, their ease of production at high efficiency and purity levels as well as their advantageous complexing and chelating properties will be discussed in the following by way of detailed examples.

1. USE OF U-230, Th-226 AND Ac-226 IN MEDICINE

The radionuclides U-230, Th-226 and Ac-226 have decay characteristics that favour their use in medical applications.

Figure 1:
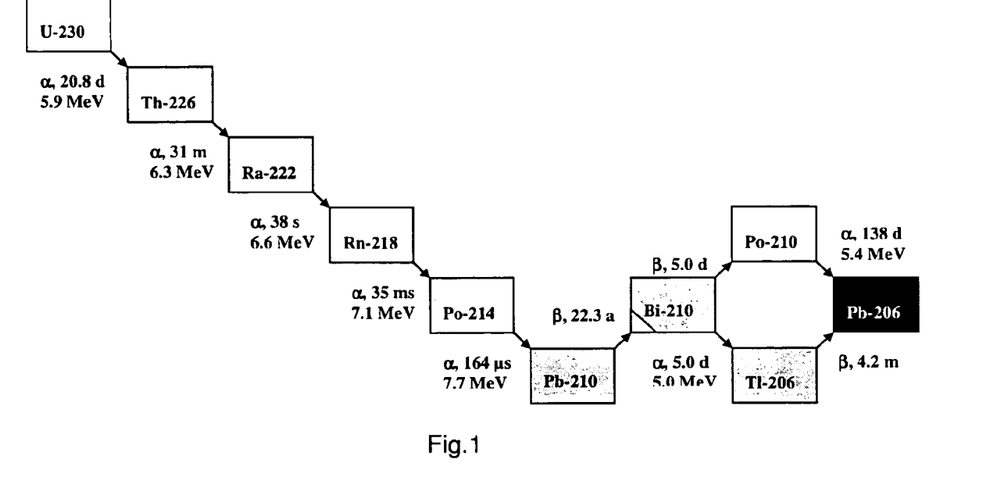
FIG. 1: is a diagram illustrating the decay chain of U-230/Th-226.

U-230 and Th-226 are alpha-emitters with half-lives of 20.8 days and 31 minutes, respectively. The decay chain of U-230 is shown in FIG. 1. Both nuclides are pure alpha-emitters that produce 5 and 4 alpha particles, respectively, with a cumulative energy of 33.6 and 27.7 MeV, until they decay to the relatively long lived beta-emitter Pb-210 (half-life: 22.3 years). All alpha-emitting daughter nuclides of Th-226 are short-lived and do not emit high-energy gamma lines that would require extensive shielding. However, Th-226 and its daughter nuclide Ra-222 emit gamma rays in the low energy range from 80-350 keV that is ideal for imaging of the biodistribution of the nuclides in the body. Th-226 and Ra-222 emit gamma rays with energy of 111 keV with an emission probability of 3.3% and with energy of 324 keV with an emission probability of 2.8%, respectively. U-230 can either be used directly for medical purposes or can be utilised as a parent nuclide for the production of Th-226. To this end U-230 can be fixed on a radionuclide generator (extraction chromatographic material or ion exchanger) that allows the selective elution of Th-226 at regular or determined time intervals.

Figure 2:
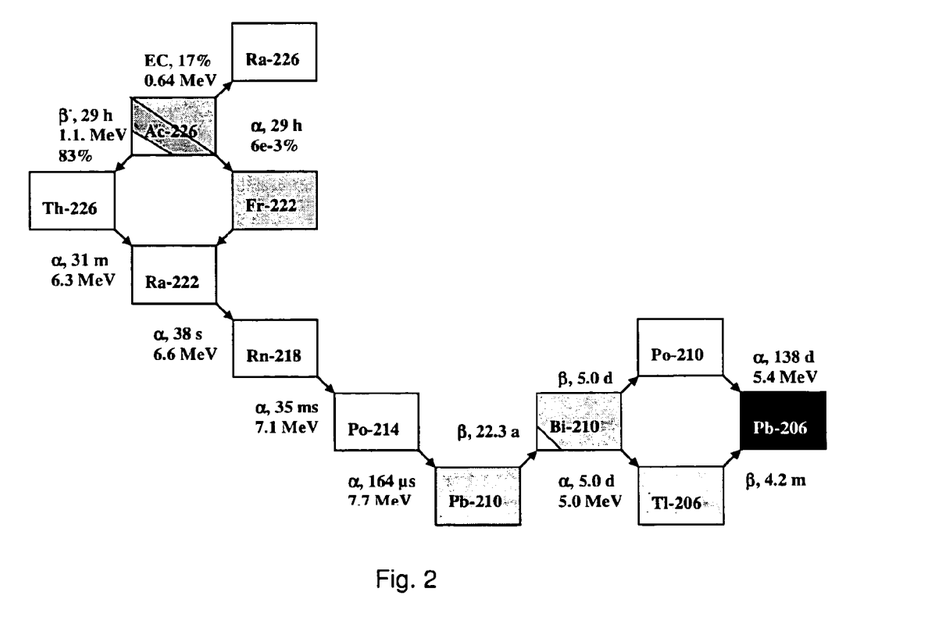
FIG. 2: is a diagram illustrating the decay chain of Ac-226.

Ac-226 has a half-life of 29 h and decays through $\beta^-$ emission with a branching ratio of 83% to Th-226. It also decays through positron emission (0.64 MeV) with a branching ratio of 17% to Ra-226 as well as through alpha-decay to Fr-222 with a low branching ratio of $6\cdot10^{-3}$%. The decay chain of Ac-226 is shown in FIG. 2. Due to the longer half-life of Ac-226 ($T_{1/2}$=29.4 hours) compared to Th-226 ($T_{1/2}$=31 min), a radiopharmaceutical containing Ac-226 can be used to target cells that are less readily accessible than in the case of using Th-226. The decay of Ac-226 will produce in situ short lived Th-226 with its favourable decay characteristics and the emission of multiple alpha-particles, resulting in the delivery of a highly cytotoxic dose to targeted cells. The distribution of Ac-226 in the body can be detected using positron emission tomography. Ac-226 can either be used directly for medical purposes or can be utilised as a mother radionuclide for the production of Th-226. To this end Ac-226 can be fixed on a radionuclide generator (extraction chromatographic material or ion exchanger) that allows the selective elution of Th-226 in regular time intervals.

2. PRODUCTION OF U-230, Ac-226 AND Th-226

Although various methods could be used to produce U-230, Ac-226 and Th-226, preferred production methods are described below.

2.1) Production of U-230 from Th-232

A first, well known production route for U-230 has been proposed by Koua Aka et al. [Ref. 13] and is based on the irradiation of natural Th-232 with protons of appropriate energy according to the reaction Th-232(p,3n)Pa-230, the obtained Pa-230 decaying into U-230. Pa-230 is a beta emitter ($\beta^+$ and $\beta^-$) with a half-life of 17.4 days that decays to U-230 with a branching ratio of 8.4%. The production of approx. 0.8 mCi of U-230 by irradiation of thick Th-232 targets has been reported by Koua Aka et al.

Two alternatives of producing U-230 by the irradiation of natural Th-232 are also proposed.

Figure 4:
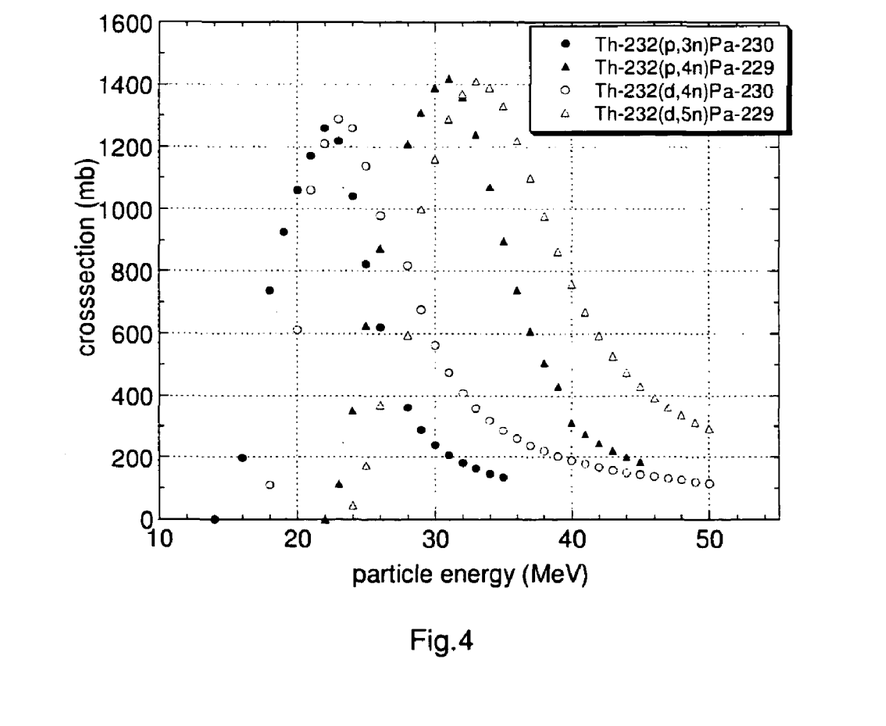
FIG. 4: is a graph showing the calculated cross-sections for the reactions Th-232(p,xn)Pa and Th-232(d,xn)Pa as function of incident particle energy (ALICE code, Lawrence Livermore National Laboratory)

According to a first alternative process, U-230 can be obtained from the decay of Pa-230 produced according to the reaction Th-232(d,4n)Pa-230. U-230 is thus indirectly obtained by the radioactive decay of Pa-230. Taking into account that according to model calculations using the ALICE code (Lawrence Livermore National Laboratory, USA), the maximum cross sections for the reaction Th-232(d,4n)Pa-230 (1290 mb at 24 MeV) is similar to the maximum cross section for the reaction Th-232(p,3n)Pa-230 (1260 mb at 22 MeV), a similar production yield can be expected using deuteron irradiation of U-230 (FIG. 4 and Table 1). The energy of the deuterons will preferably be adjusted such that the energy incident on Th-232 is between 20 and 35 MeV.

Figure 7:
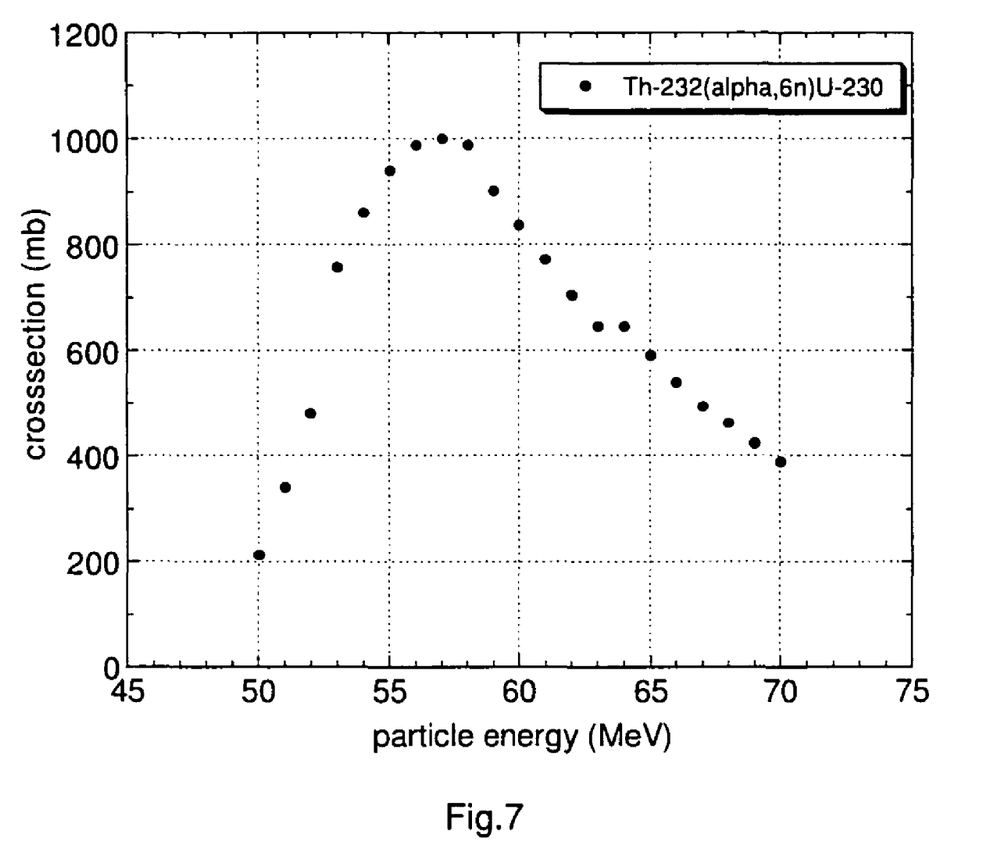
FIG. 7: is a graph showing the calculated cross-sections of the reaction Th-232($\alpha$,6n)U-230 as function of incident particle energy using the ALICE91 code (Lawrence Livermore National Laboratory).

In the second alternative process, U-230 is produced directly by irradiation of Th-232 with helium nuclei. According to the reaction Th-232($\alpha$,6n)U-230, U-230 can be produced in a direct manner. The energy of the helium particles is preferably adjusted such that the energy incident on Th-232 is between 50 and 70 MeV, more preferably between 53 and 65 MeV. Taking into account the theoretical cross sections of the reactions Th-232(p,3n)Pa-230 (1260 mb at 22 MeV) and Th-232($\alpha$,6n)U-230 (1000 mb at 57 MeV), and also taking into account that U-230 is produced directly using the latter reaction, overall a 23.6-fold enhancement of production yield can be expected using the irradiation of Th-232 by helium particles compared to the current state-of-the-art method (FIG. 7 and Table 1).

For the production of U-230 by irradiation of Th-232, preferably thorium metal will is used as target material, but also thorium targets prepared by electrode-position or thorium oxide or other suitable thorium materials can be used. The Th-232 target material is preferably placed in a capsule and/or any other suitable sealed container, e.g. made of silver or aluminium and cooled by a closed water circuit.

TABLE 1

Comparison of state-of-the-art method and present methods for the production of U-230 from Th-232.

|  | State-of-the-art (ref. 13) | Present method | Present method |
|---|---|---|---|
| Target nuclide | Th-232 | Th-232 | Th-232 |
| Nuclear reaction | Th-232(p, 3n)Pa-230 Pa-230 (8.4%) => U-230 | Th-232(d, 4n)Pa-230 Pa-230 (8.4%) => U-230 | Th-232($\alpha$, 6n)U-230 |
| Theoretical cross-section (mb) | 1260 | 1290 | 1000 |
| Particle energy (MeV) | 22 | 24 | 57 |
| Relative production yield | 1 | 1.02 | 23.6 |

It is to be noted that the production of U-230 from Th-232 by proton or deuteron irradiation may, depending on the incident proton or deuteron beam energy also lead to the production of Ac-225. Indeed, it has been observed that irradiation of Th-232 by hydrogen isotope nuclei can also be used as an alternative method for the production of Ac-225. Pa-229, obtained according to the reactions Th-232(p,4n)Pa-229 or Th-232(d,5n)Pa-229, respectively, is decaying via emission of an alpha particle with a branching ratio of 0.48% into Ac-225. The proton energy will preferably be adjusted such that the energy incident on Th-232 is between 19 and 40 MeV (FIG. 4). The deuteron energy will preferably be adjusted such that the energy incident on Th-232 is between 25 and 50 MeV (FIG. 4). Taking into account the theoretical cross sections for the reactions Th-232(p,4n)Pa-229 and Th-232(d,5n) Pa-229 as shown in FIG. 4, the production of approx. 5 $\mu$Ci Ac-225 per $\mu$Ah can be expected for the irradiation of thick Th-232 targets by protons or deuterons of the appropriate energy. As an example, by irradiation of a thick Th-232 target for 100 hours using a proton or deuteron current of 100 $\mu$A the production of approx. 50 mCi of Ac-225 can be expected.

The production of Ac-225 by irradiation of Th-232 has several important advantages over the known production methods which are based on the irradiation of Ra-226 by hydrogen nuclei. These advantages include preparation, handling and transport of targets as well as greatly reduced safety risks associated with the irradiation of low-radioactive thorium as compared to the irradiation of highly radioactive Ra-226.

2.2) Production of U-230 from Pa-231

The present invention proposes another advantageous method for producing U-230, which is based on the irradiation of Pa-231 with hydrogen isotope nuclei. This process is preferably carried out in a cyclotron, wherein the energy of the incident beam can be adjusted to optimal values. For irradiation with protons, the proton energy is preferably adjusted such that the energy incident on the Pa-231 target is between 10 and 25 MeV, more preferably between 13 and 17 MeV. For irradiation with deuterons, the deuteron energy is preferably adjusted such that the energy incident on the Pa-231 target is between 10 and 25 MeV, more preferably between 18 and 21 MeV.

Figure 3:
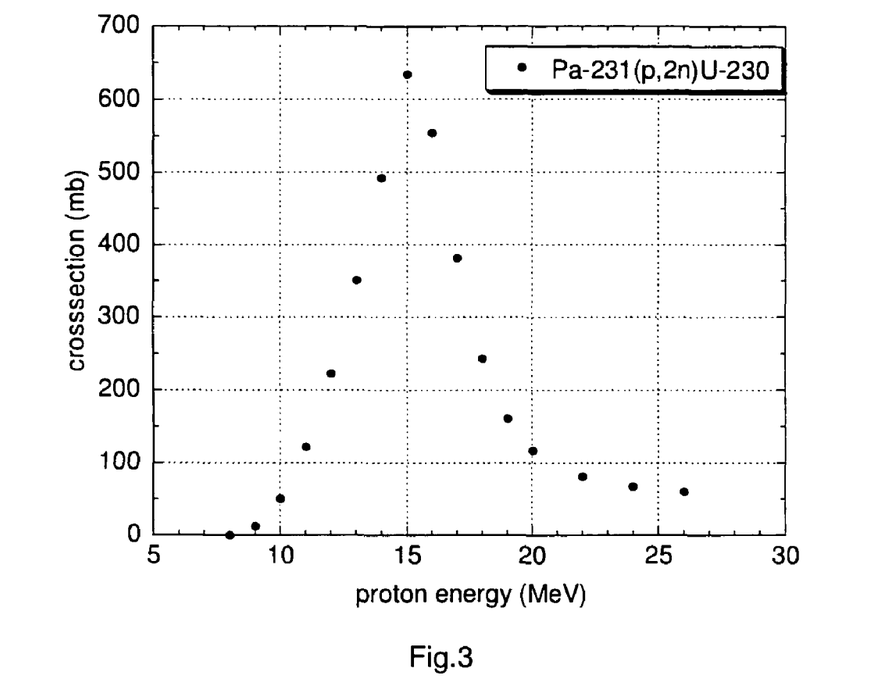
FIG. 3: is a graph showing the calculated cross-sections for the reaction Pa-231(p,2n)U-230 as function of incident proton energy (ALICE code, Lawrence Livermore National Laboratory)
Figure 5:
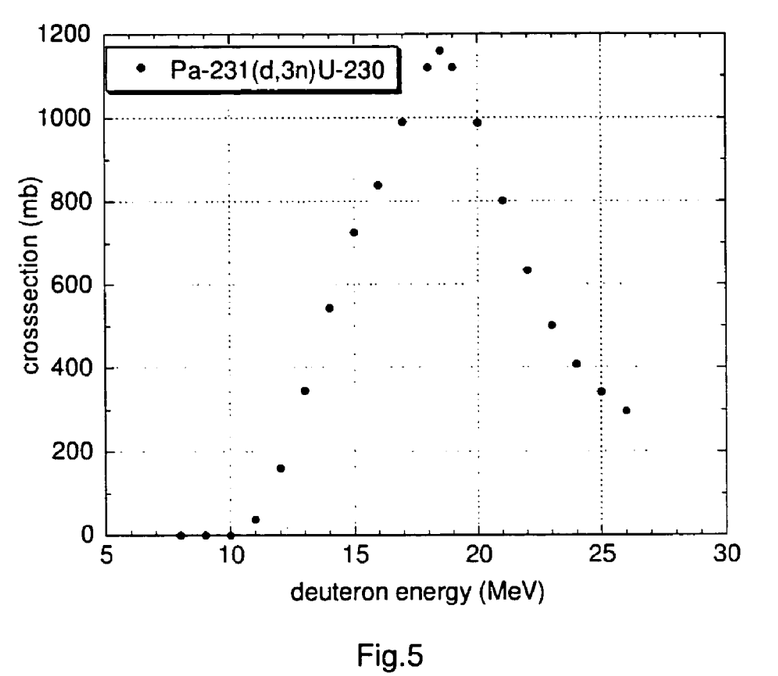
FIG. 5: is a graph showing the calculated cross-sections for the reaction Pa-231(d,3n)U-230 as function of incident deuteron energy (ALICE code, Lawrence Livermore National Laboratory)

Through the reactions proposed in this invention: Pa-231 (p,2n)U-230 and Pa-231(d,3n)U-230, U-230 can be produced directly, while through the reaction Th-232(p,3n)Pa-230, U-230 is produced only as decay product of Pa-230 with a maximal theoretical yield of 3.37 wt. % relative to the amount of Pa-230 produced. Taking into account that according to model calculations using the ALICE code (Lawrence Livermore National Laboratory, USA), the maximum cross sections for the reaction Pa-231(p,2n)U-230 (634 mb at 15 MeV, FIG. 3) is approx. 2 times lower than the maximum cross section for the reaction Th-232(p,3n)Pa-230 (1260 mb at 22 MeV, FIG. 4), overall a 14.9-fold enhancement of production yield can be expected using proton irradiation of Pa-231. The maximum cross section for the reaction Pa-231(d,3n)U-230 (1160 mb at 18.5 MeV, FIG. 5) is similar to the maximum cross-section for the reaction Th-232(p,3n)Pa-230, therefore even an overall 27.3-fold enhancement of production yield can be expected using deuteron irradiation of Pa-231 compared to the method described by Koua Aka et al. [Ref. 13] (see Table 2).

Since the direct production of U-230 by proton or deuteron irradiation of Pa-231 is expected to be approx. 15 and 27 times, respectively, more efficient than the state-of-the-art method for the production of U-230 (Ref. 13), using the production methods of the invention permits a significant increase in the amounts of U-230 and Th-226 that can be made available for pre-clinical and clinical studies. Additionally, since a significant cost factor in the production of radioisotopes in a cyclotron is related to the required irradiation time, the production methods proposed in this invention can lead to a significant reduction of production costs.

TABLE 2

Comparison of state-of-the-art method and methods proposed in this invention for the production of U-230 from Pa-231.

|  | State-of-the-art (ref. 13) | Present method | Present method |
|---|---|---|---|
| Target nuclide | Th-232 | Pa-231 | Pa-231 |
| Nuclear reaction | Th-232(p, 3n)Pa-230 Pa-230 (8.4%) => U-230 | Pa-231(p, 2n)U-230 | Pa-231(d, 3n)U-230 |
| Theoretical cross-section (mb) | 1260 | 634 | 1160 |
| Particle energy (MeV) | 22 | 15 | 18.5 |
| Relative production yield | 1 | 14.9 | 27.3 |

For irradiation, the Pa-231 target material is preferably placed in a capsule and/or any other suitable container and cooled by a closed water circuit. The protactinium may be in metallic form (e.g. electrodeposited Pa) or oxidized form. The capsule, e.g. made of silver or aluminium, provides a sealed container for the radioactive Pa-231, allows target processing after irradiation without introducing impurities into the medical grade product and avoids the introduction of undesired cations that would interfere with the chelation of the radionuclides.

After irradiation, uranium is separated from the irradiated target material, preferably by chemical separation, using e.g. conventional techniques. Chemical separation can be performed using ion exchange, extraction chromatography and/or sorption to silica gel.

It is to be noted that the fabrication and irradiation of targets containing Pa-231 requires to some extent increased safety measures compared to low-radioactive Th-232. However, the availability of suitable protactinium materials, including protactinium metal or protactinium oxide, which have a very low solubility in water, is adding an inherent safety to the irradiation process, since even in the case of target failure only minute amounts of target material would be dissolved in the cooling circuit.

2.2) Production of Ac-226

A preferred method for the production of Ac-226 is based on the irradiation of Ra-226 targets using deuterons or protons, according to the reactions Ra-226(d,2n)Ac-226 and Ra-226(p,n)Ac-226, respectively.

Figure 6:
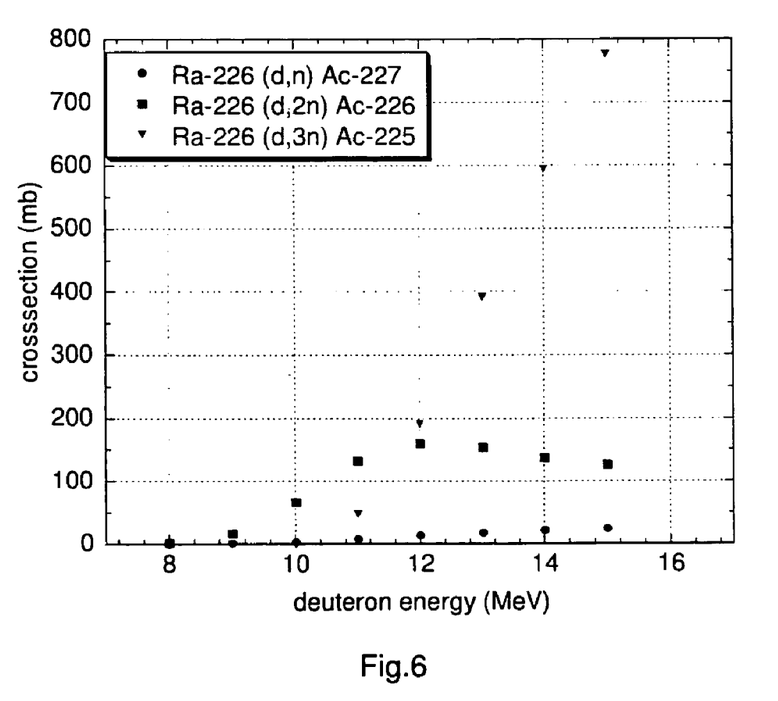
FIG. 6: is a graph showing the calculated cross-sections of the reaction Ra-226(d,xn)Ac as function of incident deuteron energy using the ALICE91 code (Lawrence Livermore National Laboratory)

Irradiation with deuterons is more preferred as it permits an increased production yield. FIG. 6 shows the calculated cross-sections of the reaction Ra-226(d,xn)Ac for the isotopes Ac-225, Ac-226 and Ac-227 in function of deuteron energy (x being equal to 1, 2 or 3 respectively). A preferred deuteron energy is between 5 and 15 MeV. However, as can be seen from the model calculations in FIG. 6, the production of Ac-226 can be expected to be enhanced with respect to other radioisotopes when the incident deuteron energy is adjusted between 10 and 12 MeV.

For irradiation with protons, the proton energy is preferably adjusted such that the energy incident on the Ra-226 target is between 5 and 15 MeV, more preferably between 8 and 12 MeV.

As is the case for U-230, the production of Ac-226 is preferably carried out in a cyclotron.

The Ra-226 target material preferably is in the form $RaCl_2$, which has been dried and pressed into pellets.

To facilitate the handling of the highly toxic Ra-226 target material, the latter is advantageously placed in a sealed capsule of silver or aluminium. If aluminium is used as capsule material, the target material is preferably placed in an envelope made of Ag, Ti or Nb before introduction into the capsule, so as to avoid contamination of the target material with aluminium, in particular during post-irradiation treatments. Ag, Ti and Nb have a high conductivity and thus allow for a high deuteron current density during irradiation. Nb is particularly preferred for its low ionising radiation emissions after irradiation.

After irradiation, actinium is preferably chemically separated from the irradiated target of Ra-226.

Separation of actinium from irradiated radium can be achieved using ion exchange or extraction chromatography, e.g. using the extraction chromatographic resin Ln-spec (by Eichrom Technologies Inc., USA). To this end the irradiated radium chloride target is dissolved in 0.01 M HCl and the resulting solution is loaded onto a column filled with Ln-spec. Subsequently radium is washed though the column using 0.1 M HCl, while actinium remains on the column. The radium eluate is conditioned to be used again for target preparation. Actinium is stripped off the column using 2 M HCl and directly loaded onto a Sr-spec (by Eichrom Technologies Inc.) column for further purification. Actinium is washed through the Sr-spec column using 2 M HCl and converted into the appropriate matrix for subsequent production of preparations for radiotherapy.

2.3) Production of Th-226

In view of the advantageous production routes proposed above, it thus appears that it is interesting to use Th-226 originating therefrom in the context of the present invention.

U-230 or Ac-226 can be used as source for Th-226. Therefore, the mother radionuclide (U-230 or Ac-226) is loaded on a separation column filled with an appropriate material, e.g. an extraction chromatographic resin or an ion exchange material that allows selective elution of Th-226 at appropriate time intervals.

Example 1

A particularly preferred U-230/Th-226 radionuclide generator is designed as follows.

U-230 is loaded onto a column containing the extraction chromatographic material TEVA® (Eichrom Technologies Inc.; this material includes as active component an aliphatic quaternary amine) from hydrochloric acid solution, e.g. 6 M hydrochloric acid. Preferentially, silica gel is used as inert support material for the extraction chromatographic material TEVA® in order to increase the radiation resistance of the generator material and to minimise its radiolytic degradation. Th-226 can be eluted from the generator using 6 M hydrochloric acid with a yield of approx. 90% in 4-6 column bed volumes, while U-230 remains on the generator. A peristaltic pump can be used for the elution of the generator to facilitate automation of the elution process.

It has been observed that more than 100 elutions of thorium using 4-6 bed volumes of 6 M HCl could be performed from a U/Th radionuclide generator consisting of TEVA® extraction chromatographic material without significant breakthrough of uranium into the thorium eluate. It will thus be appreciated that TEVA® extraction chromatographic resin, preferentially containing silica gel as inert support material, shall be advantageously used to prepare an uranium/thorium radionuclide generator.

3. PREPARATION OF RADIOPHARMACEUTICALS CONTAINING U-230, Th-226 OR Ac-226

In the following, the preparation of radiopharmaceuticals containing U-230, Th-226 or Ac-226 is treated separately for each radionuclide. As it will appear, these radiopharmaceuticals provide a broad medical application field. For illustrative purposes, the preparation of radiopharmaceuticals including these radionuclides for use in targeted radiotherapy, pre-targeted radiotherapy and for bone-targeting is described in detail, by way of example.

3.1 Preparation of U-230 Radiopharmaceuticals

As described above, separation of U-230 from irradiated Th-232 or Pa-231 targets can be performed using known chemical separation techniques, including ion exchange, extraction chromatography and sorption to silica gel.

For the preparation of radiopharmaceuticals containing U-230, purified U-230 is preferably dissolved in a first step in dilute acid, preferentially hydrochloric or nitric acid.

Example 2

A U-230 radiopharmaceutical for targeted radiotherapy is prepared as follows. The radionuclide U-230 is mixed with a buffered solution of a chelated carrier molecule in e.g. using sodium acetate buffer at pH 5-7 and incubated for an appropriate time, e.g. 1 hour. Purification of the U-230 radioconjugate can be performed using size exclusion chromatography or ion exchange procedures, followed by sterile filtration. A pharmaceutically acceptable carrier or excipient can be added and/or a scavenging agent.

Example 3

For the use of U-230 in pre-targeted radiotherapy, the radionuclide is mixed with a buffered solution of chelated biotin or another suitable carrier molecule and incubated for an appropriate time. Purification of the obtained U-230 radioconjugates can be performed using high performance liquid chromatography or ion exchange procedures and sterile filtration.

Representative conditions for forming radioconjugates are given here. To a solution containing U-230 in 0.2 M ammonium acetate, pH 5.0, containing approximately 10 mg/mL of ascorbic acid as a radioprotectant, 2 µg of chelated biotin in 1 µl of 0.2 M ammonium acetate, pH 5.0, are added. The reaction mixture is incubated for 1 h, after which 10 µl of a solution containing 1.5 mg/ml DTPA, pH 5.0, are added. The reaction mixture is incubated at room temperature for 60 min, after which radiochemical purity is determined by thin layer chromatography. A pharmaceutically acceptable carrier or excipient can be added as well as a scavenging agent.

Example 4

For the use of U-230 for bone-targeting, the solution containing U-230 will subsequently be mixed with a solution of an appropriate complexing agent to form a bone-seeking complex. Purification of the final product can be performed using ion exchange procedures and sterile filtration. The radiopharmaceutical comprising the present U-230 bone targeting complexes may further comprise a pharmaceutically acceptable carrier or excipient.

3.2 Preparation of Th-226 radiopharmaceuticals

Example 5

For the preparation of Th-226-labelled radiopharmaceuticals used for targeted alpha therapy, the eluate of Th-226 in 6 M hydrochloric acid is neutralised using sodium hydroxide, buffered to an appropriate pH value, preferentially between 5 and 7 using e.g. sodium acetate, mixed with a solution containing a chelated carrier molecule (targeting moiety) and incubated for an appropriate time, preferentially 1-5 minutes. Purification of the obtained Th-226-radioconjugates can be performed using size exclusion chromatography or ion exchange procedures and sterile filtration. The radiopharmaceutical comprising the Th-226 radioconjugates may additionally comprise a pharmaceutically acceptable carrier or excipient and/or a scavenging agent.

Representative conditions for coupling by chelation are given here: To 500 µl of Th-226-eluate in 6 M HCl, a mixture of 300 µl 10 M NaOH, 200 µl 2 M sodium acetate buffer and 100 µl of 10% ascorbic acid solution as radioprotectant is added to adjust the pH to a value of 5-6. Following addition of 100 µg of Bz-DTPA-antibody in buffered solution, the solution is incubated for 3 minutes. Subsequently 10 µl of a solution containing 1.5 mg/ml DTPA are added to quench the chelation reaction. Immediately after DTPA-addition, the radioimmunoconjugates are purified by size-exclusion chromatography and passed through a sterile filter.

Example 6

For the use of Th-226 in pre-targeted alpha therapy, the radionuclide is mixed with a buffered solution of chelated biotin or another suitable carrier molecule and incubated for an appropriate time. Purification of the Th-226-radioconjugate can be performed using ion exchange procedures and sterile filtration.

Representative conditions for coupling by chelation are given here. To a solution containing Th-226 in 0.2 M ammonium acetate, pH 5.0, containing approximately 10 mg/mL of ascorbic acid as a radioprotectant, 2 µg of Bz-DTPA-biotin in 1 µl of 0.2 M ammonium acetate, pH 5.0, are added. The reaction mixture is incubated for 3 min, after which 10 µl of a solution containing 1.5 mg/ml DTPA, pH 5.0, is added.

Immediately after DTPA-addition, the biotin targeted radioconjugate is purified and passed through a sterile filter.

Example 7

For the use of Th-226 for bone-targeting, the generator eluate containing Th-226 is neutralised, buffered and mixed with a solution of an appropriate complexing agent, e.g. phosphonic acid complexants and more specifically 1,4,7,10 tetraazacyclododecane N,N,N",N'" 1,4,7,10-tetra(methylene) phosphonic acid (DOTMP) or thorium-diethylenetriamine N,N',N" penta(methylene) phosphonic acid (DTMP), to form a bone-seeking complex. Purification of the final product can be performed using ion exchange procedures and sterile filtration.

3.3 Preparation of Ac-226 Radiopharmaceuticals

As described above, separation of Ac-226 from irradiated Ra-226 targets can be performed using known procedures of ion exchange or extraction chromatography.

For the direct use of Ac-226 in radiotherapy, purified Ac-226 will be dissolved in a first step in dilute acid, preferentially hydrochloric or nitric acid.

Example 8

For the use of Ac-226 in targeted radiotherapy, the radionuclide is mixed with a buffered solution of a chelated carrier molecule (targeting moiety) in e.g. sodium acetate buffer and incubated for an appropriate time. Purification of the Ac-226-radioconjugates can be performed using size exclusion chromatography or ion exchange procedures and sterile filtration.

Representative conditions for the chelation coupling are given here: to 150 µl of Ac-226 in 0.1 M HCl, a mixture of 40 µl of 2 M sodium acetate buffer and 10 µl of 10% ascorbic acid solution as radioprotectant is added to adjust the pH to a value of 5-6. Following addition of 100 µg of HEHA-chelated-antibody in buffered solution, the solution is incubated for 90 minutes. Subsequently 10 µl of a solution containing 1.5 mg/ml DTPA are added to quench the chelation reaction. Immediately after DTPA-addition, the radioconjugates are purified by size-exclusion chromatography and passed through a sterile filter.

Preferred conditions for a 2-step chelation coupling of Ac-226 are given here: $^{226}$Ac (in 25 µL 0.2 mol/L HCl) is incubated with I-ascorbic acid (150 g/L, 20 µL), 2-(p-isothiocyanatobenzyl)-1,4,7,10-tetraazacyclododecane-1,4,7,10-tetraacetic acid (DOTA-NCS) (10 g/L, 50 µL), and tetramethylammonium acetate (2 mol/L, 50 µL) to facilitate incorporation of $^{226}$AC into DOTA. The reaction is allowed to continue for 30 min at 60° C. (pH 5.0). For conjugation of $^{226}$Ac-DOTA to the antibody (the second-step reaction), another 20 µL of ascorbic acid are added before adding 1 mg of antibody (200 µL). The pH is adjusted with carbonate/bicarbonate buffer (1 mol/L, 100 µL) to 9.0 and incubation is for 30 min at 37° C. Subsequently free $^{226}$AC along with other metals is absorbed with 20 µL 10 mmol/L diethylenetriaminepentaacetic acid (DTPA) and the unconjugated $^{226}$Ac is separated from the $^{226}$Ac-radioconjugates by PD10 size exclusion (Bio-Rad) using 1% human serum albumin in 0.9% saline as eluent. Quality control of the final product can include thin-layer chromatography to determine radiopurity, a cell-based binding assay to measure immunoreactivity of the antibody vehicle, Limulus amebocyte lysate testing to determine pyrogen content, and microbiologic culture in fluid thioglycollate of soybean-casein digest medium to verify sterility.

Example 9

For the use of Ac-226 in pre-targeted radiotherapy, the radionuclide is mixed with a buffered solution of chelated biotin or another suitable carrier molecule and incubated for an appropriate time. Purification of the Ac-226-radioconjugates can be performed using ion exchange procedures and sterile filtration.

Representative conditions for chelation coupling are given here. To a solution containing Ac-226 in 0.2 M ammonium acetate, pH 5.0, containing approximately 10 mg/mL of ascorbic acid as a radioprotectant, 2 µg of HEHA-biotin in 1 µl of 0.2 M ammonium acetate, pH 5.0, are added. The reaction mixture is incubated for 90 min, after which 10 µl of a solution containing 1.5 mg/ml DTPA, pH 6.0, is added. Immediately after DTPA-addition, the biotin radioconjugates are purified and passed through a sterile filter.

Alternative conditions for chelation coupling of Ac-226 are given here:

Twenty microliters to 100 µL carrier-free Ac-226 in 0.05 M HCl is diluted with 2 M ammonium acetate, pH 5, to a total volume of 0.25 mL, and 1 mg DOTA-biotin is added. The solution is heated for 30 minutes at 80° C. followed by the addition of 25 µL 100 mM DTPA to chelate any unbound radioisotope. Radio-chemical purity is determined by $C_{18}$ reverse-phase gradient high-performance liquid chromatography (HPLC) with flow-through gamma detection.

Example 10

For the use of Ac-226 for bone-targeting, the solution containing Ac-226 is subsequently mixed with a solution of an appropriate complexing agent to form bone-seeking complexes. Suitable bone-seeking chelating and/or complexing molecules include, but are not limited to, phosphonic acid complexants, e.g. 1,4,7,10 tetraazacyclododecane N,N',N", N'" 1,4,7,10-tetra(methylene) phosphonic acid (DOTMP) as described in [Ref. 8]. If required, purification of the final product can be performed using ion exchange procedures and sterile filtration.

4. CHELATING AND COMPLEXING MOLECULES FOR BINDING OF U-230, Ac-226 AND Th-226

The coupling of Th-226, Ac-226 and/or U-230 to the targeting moiety can be done in any suitable way, as long as the target specificity of the targeting moiety is not substantially reduced. Suitable complexing or chelating molecules that can be used to bind Th-226, Ac-226 and/or U-230 to targeting moieties such as biological carrier molecules (e.g. monoclonal antibodies, humanized antibodies, antibody fragments or peptides) or carrier molecules for pre-targeted radiotherapy (e.g. biotin) are widely described in the literature.

When U-230 is used in targeted or pre-targeted radiotherapy, preferentially a chelating molecule (agent) should be used that binds uranium as well as its daughter nuclide thorium in a stable manner, in order to minimise the dislocation of Th-226 from the target cell following its formation through the decay of U-230 in situ. Possible chelating molecules that can be used to bind uranium and thorium include multidentate ligands containing catecholate, catecholamide or hydroxypyridinone units as described in [Ref. 7], e.g. 5-LIO(Me-3,2-HOPO), 5-LICAM(S), 3,4,3-LI(1,2-HOPO) as described in [Ref. 6] and 5-LI(Me-3,2-HOPO) [Ref. 7].

Analogously, when Ac-226 is used in targeted or pre-targeted radiotherapy, preferentially a chelating molecule should be used that binds actinium as well as its daughter nuclide thorium in a stable manner, in order to minimise the dislocation of Th-226 from the target cell following its formation through the decay of Ac-226 in situ.

The following chelating molecules are given as examples:

DTPA (diethylenetriaminepentaacetic acid) and its derivatives (e.g. benzyl-DTPA, MX-DTPA (tiuxetan), cyclohexyl-DTPA), preferentially for chelation of thorium;

DOTA (1,4,7,10-tetraazacyclododecane-N,N',N'',N'''-tetraacetic acid) and its derivatives, preferentially for chelation of actinium;

HEHA (1,4,7,10,13,16-hexaazacyclooctadecane-N,N',N'', N''',N'''',N'''''-hexaacetic acid) and its derivatives, preferentially for chelation of actinium and thorium;

OHEC (octaazacyclohexacosane-1,4,7,10,14,17,20,23-octaacetate) and its derivatives, preferentially for chelation of actinium and thorium;

multidentate ligands containing catecholate, catecholamide or hydroxypyridinone units as described in [Ref. 7], e.g. 5-LIO(Me-3,2-HOPO), 5-LICAM(S), 3,4,3-LI (1,2-HOPO) as described in [Ref. 6] and 5-LI(Me-3,2-HOPO) [Ref. 7];

calixarene systems, crown ethers;

molecules that are studied as sequestering agents for tri-, tetra- and hexavalent actinides as described in [Ref. 7].

Example 11

For application in the present invention, the binding of actinium and/or thorium to antibody constructs chelated with HEHA and derivatives of DTPA, respectively, and their stability in human blood serum has been studied.

Monoclonal antibodies chelated with benzyl-DTPA and cyclohexyl-DTPA, respectively, were coupled to Th-227, used as chemical analog of Th-226. In a typical experiment, 0.5 ml of Th-benzyl-DTPA-antibody radioconjugate or Th-cyclohexyl-DTPA-antibody radioconjugate, respectively, were added to 1.0 ml of human blood serum at 37° C. and kept under 5% $CO_2$-atmosphere. At appropriate time points the fractions of thorium bound to the antibody and released from the antibody, respectively, were analysed by thin layer liquid chromatography using 0.05 M EDTA as solvent. As summarized in Table 3, the Th-benzyl-DTPA-antibody radioconjugate (denoted RC1) as well as the Th-cyclohexyl-DTPA-antibody radioconjugate (denoted RC2) showed excellent stability in human blood serum. After 5 hours incubation in human blood serum, only negligible fractions of thorium were released from the antibody construct. Considering the half-life of Th-226 ($T_{1/2}$=31 min), the data show that thorium will remain bound to the antibody-construct for a time period exceeding 10 half-lives, resulting in virtually complete decay of Th-226 while bound to the antibody. Therefore derivatives of DTPA are recommended as excellent chelators for the coupling (or binding) of thorium to targeting moieties.

TABLE 3

Stability of the radioconjugates RC1 and RC2 in human blood serum at 37° C.

| Time (min) | RC1 - Th released (%)* | RC2 - Th released (%)* |
|---|---|---|
| 5 | 1 | 4 |
| 15 | n/a | 3 |
| 30 | 2 | 3 |
| 60 | 1 | 4 |
| 120 | 2 | 4 |
| 180 | 1 | 4 |

TABLE 3-continued

Stability of the radioconjugates RC1 and RC2 in human blood serum at 37° C.

| Time (min) | RC1 - Th released (%)* | RC2 - Th released (%)* |
|---|---|---|
| 210 | n/a | 3 |
| 240 | 2 | 4 |
| 270 | n/a | 3 |
| 300 | 4 | 3 |

(n/a: not analysed; *combined uncertainty of the measurement +/− 4%).

Example 12

In an analogous experiment, monoclonal antibodies chelated with HEHA were labelled using Th-227 as chemical analog of Th-226. In a typical experiment, 0.5 ml of Th-HEHA-antibody construct were added to 1.0 ml of human blood serum at 37° C. and kept under 5% $CO_2$-atmosphere. At appropriate time points the fractions of thorium bound to the antibody and released from the antibody, respectively, were analysed by thin layer liquid chromatography using 0.05 M EDTA as solvent. As summarized in Table 4, the Th-HEHA-antibody radioconjugate (denoted RC3) showed moderate stability in human blood serum. After 5 hours incubation in human blood serum, approx. 30% of thorium were released from the antibody construct. Considering the half-life of Th-226 ($T_{1/2}$=31 min), the data show that approx. 70% of thorium will remain bound to the antibody-construct for a time period exceeding 10 half-lives. Therefore HEHA may be used as chelator for linking of thorium to targeting moieties.

TABLE 4

Stability of the RC3 radioconjugate in human blood serum at 37° C.

| Time (min) | RC3 - Th released (%)* |
|---|---|
| 5 | 9 |
| 45 | 18 |
| 90 | 20 |
| 160 | 24 |
| 260 | 27 |
| 310 | 31 |

(*combined uncertainty of the measurement +/− 4%).

Example 13

To study the stability of actinium radioimmunoconjugates in human blood serum, monoclonal antibodies chelated with HEHA were labelled using Ac-225 as chemical analog of Ac-226. In a typical experiment, 0.5 ml of Ac-HEHA-antibody radioconjugates were added to 1.0 ml of human blood serum at 37° C. and kept under 5% $CO_2$-atmosphere. At appropriate time points the fractions of actinium bound to the antibody and released from the antibody, respectively, were analysed by thin layer liquid chromatography using 0.05 M EDTA as solvent. As summarized in Table 5, the Ac-HEHA-antibody radioconjugate (denoted RC4) showed sufficient stability in human blood serum. After 145 hours incubation in human blood serum, corresponding to 5 half-lives of Ac-226, only approx. 20% of total actinium activity were released from the radioconjugate. The use of HEHA for the linking of Ac-225 to targeting moieties is widely described in the literature and is proposed as an advantageous chelating agent of Ac-226 in the frame of this invention.

Hence, it has been found that HEHA binds actinium and thorium in a relatively stable manner. Accordingly, the present invention also proposes the use of HEHA to bind Ac-226 to targeting moieties, since it is of particular advantage in order to minimise dislocation of the in situ produced Th-226 from the target site.

TABLE 5

Stability of the radioconjugate RC4 in human blood serum at 37° C.

| Time (hours) | RC4 - Ac released (%)* |
|---|---|
| 0.1 | 4 |
| 0.5 | 8 |
| 1 | 8 |
| 2 | 14 |
| 24 | 21 |
| 40 | 14 |
| 43 | 18 |
| 45 | 18 |
| 48 | 15 |
| 65 | 19 |
| 67 | 20 |
| 70 | 19 |
| 137 | 17 |
| 143 | 20 |

(*combined uncertainty of the measurement +/− 4%).

5. LIST OF REFERENCES (1) Allen, B., Li, Y., Rizvi, S., Russell, P. J., 2003. Targeted alpha therapy of prostate cancer. Methods Mol. Med. 81, 333-357.

(2) Apostolidis, Ch., Carlos-Marquez, R., Janssens, W., Molinet, R., Nikula, T., Ouadi, A., 2001. Cancer treatment using Bi-213 and Ac-225 in radioimmunotherapy. Nucl. News 44 (13) 29-33.

(4) Boll, R. A., Malkemus, D. W., Mirzadeh, S., 2003. Production of Ac-225 for alpha-particle-mediated radioimmunotherapy. Proc. 225th ACS National Meeting, New Orleans, USA, March 23-27.

(5) Dadachova, E., Bryan, R. A., Frenkel, A., Zhang, T., Apostolidis, C., Nosanchuk, J. S., Nosanchuk, J. D., Casadevall, A., 2004. Evaluation of acute hematological and long term pulmonary toxicity of radioimmunotherapy of Cryptococcus neoformans infection in murine models, Antimicrob. Agents Chemother. 48(3), 1004-6.

(6) Durbin, P. W., Kullgren, B., Ebbe, S. N., Xu, J., Raymond, K. N., 2000. Chelating agents for uranium(VI): 2. Efficacy and toxicity of tetradentate catecholate and hydroxypyridinonate ligands in mice. Health Phys. 78(5), 511-521

(7) Gordon, A. E. V., Xu, J., Raymond, K. N., 2003: Rational design of sequestering agents for plutonium and other actinides. Chem. Rev. 103, 4207-4282.

(8) Henriksen G., Bruland O, S., Larsen R. H., 2004: Thorium and actinium polyphosphonate compounds as bone-seeking alpha particle-emitting agents. Anticancer Res. 24(1): 101-5.

(9) Huber, R., Seidl, Ch., Schmid, E., Seidenschwang, S., Becker, K.-F., Schuhmacher, Ch., Apostolidis, C., Nikula, T., Kremmer, E., Schwaiger, M., Senekowitsch-Schmidtke, R., 2003. Locoregional α-radioimmunotherapy of intraperitoneal tumor cell dissemination using a tumor-specific monoclonal antibody. Clin. Canc. Res. 9, 3922-3928.

(10) Mertens W C, Filipczak L A, Ben-Josef E, Davis L P, Porter A T.: Systemic bone-seeking radionuclides for palliation of painful osseous metastases: current concepts. CA Cancer J Clin. 1998 November-December; 48(6):361-74, 321.

(11) Jurcic, J. G., Larson, S. M., Sgouros, G., McDevitt, M., Finn, R. D., Divgi, C. R., Ballangrud, A. M., Hamacher, K. A., Ma, D., Humm, J. L., Brechbiel, M. W., Molinet, R., Scheinberg, D. A., 2002. Targeted α-particle immunotherapy for myeloid leukemia. Blood 100 (4), 1233-1239.

(12) Kennel, S. J., Lankford, T., Davern, S., Foote, L., Taniguchi, K., Ohizumi, I., Tsutsumi, Y., Nakagawa, S., Mayumi, T., Mirzadeh, S., 2002. Therapy of rat tracheal carcinoma IC-12 in SCID mice: vascular targeting with [213Bi]-MAb TES-23. Eur J Cancer. 38(9),1278-12.

(13) Koua Aka, A., Barci, V., Ardisson, G., Righetti, R., Le Du, J. F., Trubert, D., 1995. Reinvestigation of decay properties of nuclei belonging to the U-230 series using continuous radiochemical separations. Radiochim. Acta 68, 155-160.

(14) Lloyd R D, Mays C W, Taylor G N, Atherton D R, Bruenger F W, Jones C W.: Radium-224 retention, distribution, and dosimetry in beagles. Radiat Res. 1982 November; 92(2):280-95.

(15) Pagel, J. M., Hedin, N., Subbiah, K., Meyer, D., Mallet, R., Axworthy, D., Theodore, L. J., Wilbur, D. S., Matthews, D. C., Press, O. W., 2003: Comparison of anti-CD-20 and anti-CD45 antibodies for conventional and pretargeted radioimmunotherapy of B-cell lymphomas. Blood 102(6), 2340-2348.

(16) Vandenbulcke, K., De Vos, F., Offner, F., Philippe, J., Apostolidis, Ch., Molinet, R., Nikula, T., Bacher, K., De Gelder, V., Vral, A., Lahorte, Ch., Thierens, H., Dierckx, R. A., Slegers, G., 2003. In vitro evaluation of 213Bi-rituximab versus external gamma radiation for the treatment of B-CLL patients: relative biological efficacy with respect to apoptosis induction and chromosomal damage. Eur. J. Nucl. Med. Mol. Imaging. 30 (10), 1357-1364.

(17) Weiden, P. L., Breitz, H. B., 2001: Pretargeted radioimmunotherapy (PRIT) for treatment of non-Hodgkin's lymphoma (NHL). Crit. Rev. Oncol./Hemat. 40, 37-51.

(18) Zhang, M., Yao, Z., Garmestani, K., Axworthy, D. B., Zhang, Z., Mallet, R. W., Theodore, L. J., Goldman, C. K., Brechbiel, M. W., Carrasquillo, J. A., Waldmann, T. A., 2002: Pretargeting radioimmunotherapy of a murine model of adult T-cell leukemia with the α-emitting radionuclide bismuth-213. Blood 100(1), 208-216.

(19) Hassfjell S P, Bruland O S, Hoff P.: 212Bi-DOTMP: an alpha particle emitting bone-seeking agent for targeted radiotherapy. Nucl Med. Biol. 1997 April; 24(3):231-7.

(20) Howell R W, Goddu S M, Narra V R, Fisher D R, Schenter R E, Rao D V.: Radiotoxicity of gadolinium-148 and radium-223 in mouse testes: relative biological effectiveness of alpha-particle emitters in vivo. Radiat Res. 1997 March; 147(3):342-8.

(21) Larsen R H, Murud K M, Akabani G, Hoff P, Bruland O S, Zalutsky M R.: 211At- and 131I-labeled bisphosphonates with high in vivo stability and bone accumulation. J Nucl Med. 1999 July; 40(7):1197-203.

(22) Le Doussal J M, Gruaz-Guyon A, Martin M, Gautherot E, Delaage M, Barbet J.: Targeting of indium 111-labeled bivalent hapten to human melanoma mediated by bispecific monoclonal antibody conjugates: imaging of tumors hosted in nude mice. Cancer Res. 1990 Jun. 1; 50(11): 3445-52.

(25) Paganelli G, Magnani P, Zito F, Villa E, Sudati F, Lopalco L, Rossetti C, Malcovati M, Chiolerio F, Seccamani E, et al.: Three-step monoclonal antibody tumor targeting in carcinoembryonic antigen-positive patients. Cancer Res. 1991 Nov. 1; 51(21):5960-6

(26) Paganelli G, Bartolomei M, Ferrari M, Cremonesi M, Broggi G, Maira G, Sturiale C, Grana C, Prisco G, Gatti M, Caliceti P, Chinol M.: Pre-targeted locoregional radioimmunotherapy with 90Y-biotin in glioma patients: phase I study and preliminary therapeutic results. Cancer Biother Radiopharm. 2001 June; 16(3):227-35.

The invention claimed is:

1. A method for treating cancer by alpha-radioimmunotherapy comprising:
    administering to a subject in need thereof an effective amount of a radioconjugate comprising:
    a targeting moiety having a binding specificity for cancer cell, and
    one or more radionuclides selected from the group consisting of Th-226 or U-230;
    wherein said targeting moiety binds to the cancer cell thus exposing the cancer cell to a therapeutically effective number of alpha particles which are released by natural radioactive decay of Th-226 or U-230, and thus treating the cancer.

2. The method of claim 1, wherein said targeting moiety binds directly to the cancer cell.

3. The method of claim 1, wherein said cancer cell has been exposed to a pretargeting agent.

4. The method according to claim 1, wherein said targeting moiety is selected form the group consisting of an antibody, an antibody fragment, and a peptide.

5. The method according to claim 1, wherein said targeting moiety is a ligand for a cell surface receptor or a fragment thereof.

6. The method according to claim 5, wherein said targeting moiety is a ligand and said ligand binding site comprises a cell-surface receptor.

7. The method according to claim 1, wherein said targeting moiety is a monoclonal antibody or a monoclonal antibody fragment.

8. The method according to claim 1, wherein a plurality of said radionuclides are bound to a carrier and said carrier is coupled to said targeting moiety.

9. The method of claim 1, wherein the targeting moiety is bound to the radionuclide by a chelating agent.

10. The method of claim 1, wherein one or more radionuclides are bound to a carrier which is bound to one or more targeting moieties.

11. The method of claim 1, wherein said cancer cell has been exposed to a pretargeting moiety that is an avidin-based compound.

12. A method for selectively killing a cell by alpha-radioimmunotherapy comprising:
    administering to a subject in need thereof an effective amount of a radioconjugate comprising:
    a targeting moiety, and
    a radionuclide which is Th-226 or U-230;
    wherein said radioconjugate binds to the cell and releases alpha particles by natural radioactive decay.

* * * * *